(12) United States Patent
Baekgaard et al.

(10) Patent No.: US 7,006,638 B1
(45) Date of Patent: Feb. 28, 2006

(54) ELECTRONIC STETHOSCOPE

(75) Inventors: Knud Erik Baekgaard, Holstebro (DK); Torben Naurbo Dalgaard, Holstebro (DK)

(73) Assignee: Bang & Olufsen Technology A/S, Struer (DK)

( * ) Notice: Subject to any disclaimer, the term of this patent is extended or adjusted under 35 U.S.C. 154(b) by 536 days.

(21) Appl. No.: 09/688,216

(22) Filed: Oct. 16, 2000

Related U.S. Application Data

(63) Continuation-in-part of application No. 08/793,622, filed on Feb. 28, 1997, now Pat. No. 6,134,331.

(30) Foreign Application Priority Data

Aug. 30, 1994 (DK) ..................................... 1005/94

(51) Int. Cl.
*A61B 7/04* (2006.01)
(52) U.S. Cl. ........................................................ 381/67
(58) Field of Classification Search ................. 381/67, 381/71.6, 99; 600/528
See application file for complete search history.

(56) References Cited

U.S. PATENT DOCUMENTS

| | | | | |
|---|---|---|---|---|
| 3,943,304 A | * | 3/1976 | Piribauer | ..................... 381/182 |
| 4,425,481 A | | 1/1984 | Mansgold et al. | |
| 4,534,058 A | * | 8/1985 | Hower | ......................... 381/67 |
| 4,594,731 A | | 6/1986 | Lewkowicz | |
| 4,598,417 A | | 7/1986 | Deno | |
| 4,770,189 A | * | 9/1988 | Shyu | ........................... 600/586 |
| 4,783,814 A | | 11/1988 | Foley | |
| 5,003,605 A | | 3/1991 | Phillipps et al. | |
| 5,008,939 A | * | 4/1991 | Bose et al. | .................... 381/15 |
| 5,347,583 A | * | 9/1994 | Dieken et al. | ................. 381/67 |
| 5,481,615 A | | 1/1996 | Eatwell et al. | |
| 5,492,129 A | * | 2/1996 | Greenberger | ............... 600/528 |
| 5,539,831 A | | 7/1996 | Harley | |
| 5,557,681 A | * | 9/1996 | Thomasson | .................. 327/553 |
| 5,602,924 A | | 2/1997 | Durand et al. | |
| 5,610,987 A | * | 3/1997 | Harley | ......................... 381/114 |
| 6,134,331 A | * | 10/2000 | B.ae butted.kgaard | ....... 381/67 |
| 6,219,424 B1 | * | 4/2001 | Murphy | ......................... 381/67 |
| 6,807,280 B1 | * | 10/2004 | Stroud et al. | ................. 381/106 |

OTHER PUBLICATIONS

HRTF Measurements of a Kemar Dummy-Head Microphone, Bill Gardner et al., Mit Media Lab, HTTP://sound-.media.mit.edu/KEMAR/hrtfdoc.txt, Aug. 8, 2000, 9 pages.

* cited by examiner

*Primary Examiner*—Laura A. Grier
(74) *Attorney, Agent, or Firm*—David S. Safran

(57) ABSTRACT

An electronic stethoscope having a vibration transducer, an amplifier, a headphone arrangement, and at least one digital filter for establishing at least one impulse transfer function corresponding to at least one acoustic stethoscope type. Thus, the signals heard will correspond to those learned, and thereby the advantages of greater amplification and elimination of noise sources may be fully utilized. The ability to compensate for an individual doctor's hearing loss is enabled. Furthermore, with stereoscopic embodiments, sound frequency distributions can be transformed to spatial or temporal sound distributions perceivable by the user facilitating, for example, the detection of heart murmurs and the taking of blood pressure.

18 Claims, 5 Drawing Sheets

Synthesis

Analysis

ELECTRONIC STETHOSCOPE

CROSS REFERENCE TO RELATED APPLICATION

This application is a continuation-in-part of co-pending U.S. patent application Ser. No. 08/793,622.

BACKGROUND OF THE INVENTION

1. Field of the Invention

The invention relates to an electronic stethoscope of the type comprising a vibration transducer, an amplifier, and a headphone arrangement.

2. Description of Related Art

Stethoscopes are used by physicians to listen to sounds from the organism, in particular heart and lungs. The phenomena listened for emit sounds with frequencies from below 16 Hz to about 8 kHz, but a serious low pass filtering occurs during the passage of tissue and skin. The skin acts like a transmitter of those signals which are subsequently accessible. The construction of the stethoscope ascertains that only a small area of the skin is listened to at a time, and that sounds in the room outside are dampened, and thus, the signal-to-noise ratio is somewhat improved. Physicians train actively in the use of stethoscopes, and thereby their ability to distinguish signals in the surrounding noise may rise by about 15 dB. This occurs the world over, and one might say that a stethoscope is a universal tool. However, its value and/or performance to the users have fallen, due to the technical development of society. The increased machine noise, in particular in hospitals, in practice, causes the signals to lie below, or at the most at, the lower limit of human hearing. To this may be added that more and more young persons suffer from hearing loss at the time they may embark on a medical education, and hence the acoustic stethoscope has in practice reached its limit of performance.

It has long been realized that a traditional acoustic stethoscope introduces many linear distortions in its signal transmission, in particular because of the possibility for standing waves in the long tubes. This may be expressed differently by stating that the bad impulse response causes a strong distortion of the temporal reproduction of the signals. Traditionally, there are various constructions of stethoscopes, and they each have their individual characteristic transfer function, and one may to a certain degree, by changing acoustical stethoscope, obtain a more distinct representation of a given acoustic phenomenon. However, the physician's reliability in using stethoscopes is generally so large, in particular when using the stethoscope they have become used to, that the impulse response problem has not been regarded as a bar to the use of acoustic stethoscopes.

For this reason, it has not been attractive to use an electronic stethoscope, even though it gives the possibility of active amplification to any desired degree. Even though there are furthermore very improved possibilities for adapting the sensitivity of a vibration transducer to the body being measured upon, and even though headphones with a high damping may act as better insulators against surrounding noise than ordinary earpieces of a traditional stethoscope, an electronic stethoscope still meets resistance, in particular because it does not "sound like what they used to," due to the wider frequency band and the consequent larger content of noise. The ability to distinguish phenomena which has laboriously been learnt by the physician does not help any longer.

It has been recognized that there is a need for amplifying certain frequency areas relative to those which are effectively reproduced by an acoustic stethoscope. A known construction of an electronic stethoscope is described in U.S. Pat. No. 5,003,605 which electronically performs a lifting of these wider frequency areas and performs a frequency conversion for very low frequency areas. In this way certain phenomena are given an improved clarity. Furthermore, the stethoscope is connected to electrodes and electrocardiographic circuits for the recognition of the QRS complex in order that signals representing the electrical activity of the heart may be brought to the ear simultaneously with the heart sounds so that the temporal relationship of the sounds in relation to the heart cycle may be evaluated.

Other example of an electronic stethoscope can be found in U.S. Pat. No. 4,598,417. In the stethoscope of this patent, a signal processing approach is used which relies upon an acousto-electronic feedback to provide an error or adjustment signal to amplifier gain control circuits. However, such a stethoscope is complex, prone to failure, and expensive to produce. For example, the feedback signal processing approach requires a second microphone and associated electronics for monitoring the sound output of the electronic stethoscope. Furthermore, the feedback microphone wold be prone to performance degradation (e.g., change in frequency response, sensitivity, etc.) over time from either natural aging, exposure to harsh environments and/or abuse by the user. Such performance degradation of the microphone would, in turn, degrade the performance of the device.

Crude attempts have been made to provide a digital stethoscope in which the sound is presented to two ears in a binaural fashion creating a synthetic listening space in which the audible phenomena of interest are distributed spectrally from left to right in order that lower frequencies appear to emanate from one side and higher frequencies from the other side via analog means. U.S. Pat. No. 4,594,731 describes the generation of higher and more audible frequencies from the actual cardiac sounds by means of frequency multipliers, and these sounds are then subjected to an artificial shift left-to-right in the stereo image by means of reciprocal ramp-shaped control signals. It appears that the results obtained are inextricably linked to the simultaneous use of these two principles. However, a physician desiring to use this type of apparatus will first have to learn to listen for completely new sounds and will then have to accommodate the stereophonic signal which for each cycle of synthetic cardiac sounds is similar to turning the balance control on a stereo amplifier from left to right. In U.S. Pat. No. 4,783,814 use is made of a variable time delay to provide signals to left and right ears which have a time delay between them, in order to enable the physician to distinguish time intervals which are less than 40 ms apart. The sounds gain a distinct quality in that the physician perceives a spatial orientation to the sound that is as if the heart sounds come from within his own head. However, neither of these known attempts provide realism to the heart sound, and the sounds produced are so different from the sounds that physicians have been trained to recognize that improved signal processing is necessary to make realistic use of binaural ausculation.

It has also been known since around 1994 that the brain is able to process sounds more effectively when it receives slightly different input from each of the two ears. This fact has been used to improve audio reproduction of music and for films, i.e., stereo and surround sound vs. monaural sound. This ability has also been used by jet airplane pilots to increase separation when listening to several communication channels simultaneously. The use of special fitters for these purposes is known and research has been conducted to determine the filter effect of the head (characterized as Head related Transfer Functions, HRTF=s) with regard to sound from two microphones based on the distance and source; see, *HRTF Measurements of a KEMAR Dummy-Head Microphone*, Bill Gardner and Keith Martin, MIT Media Lab *Perceptual Computing—Technical Report #280*, May, 1984, which can be found on the website of the Massachusetts Institute of Technology. However, to date, no known attempt has been made to use this ability in an electronic stethoscope to separate or transform defined sound components so as to present different features to each of the physician's ears.

SUMMARY OF THE INVENTION

It has been recognized in the invention that it will be possible to obtain a considerably improved stethoscope which has both the advantage of a larger amplification and of knowledgeable analysis by a physician, who will not be confused by a changed sound characteristic, provided that there is in the signal path of an otherwise linear electronic stethoscope connected a filter with an impulse transfer function which corresponds to at least one known acoustic stethoscope. This means that temporal relationships are now reproduced as if they were transmitted through the said acoustic stethoscope. Thus, there is in a very advantageous manner obtained an interaction between man and auxiliary equipment. By an A/B comparison between the linear sound and the simulated stethoscope sound certain phenomena may be recognized which were not as clear in traditional stethoscopy. Furthermore there is a possibility to permit physicians to discuss the same phenomenon during simultaneous auscultation, as several headphones may well be connected to one and the same amplifier with filter.

With the access to modern technology it is obvious that digital filtering will be used, because it permits reprogramming without lengthy calibration. This also opens possibilities for letting the electronic stethoscope store filter transfer functions which correspond to the known main types of stethoscopes (small and large cup, with or without membrane) in order that the physician using it has only to select the filter function which corresponds best to the type of stethoscope at this particular physician has the best training in—or which according to traditional teaching is found as best suited to the task. In this respect it will also be feasible to let digital signal processing adapt the filter to the signal whereby a real improvement in the signal-to-noise ratio is obtained.

While using digital signal processing the stethoscope according to an embodiment of the invention contains pattern recognition means for the acoustic signal for adaptive reduction of noise from the surroundings as well as suppression of repetitive signals in the auscultated signal. Hereby, e.g., the sound of heartbeats may be reduced when auscultating lungs, or the heart sound of the mother may be reduced while performing fetal auscultation.

Similarly a further embodiment establishes a reference to the heart sound, in that the pattern recognition means are used for eliminating, respective enhancing parts of repetitive signals in the signal listened to. Thus, it becomes possible to diagnose sounds due to disease in the heart and surrounding arteries, and a "windowing function" is enabled where only part of a heart cycle is listened to, e.g. the systole. Correspondingly one may synchronize to the respiration when performing examination of the respiratory passages/lungs.

In that it has been realized in the invention that it is possible and extremely advantageous to perform signal processing in the passage from transducer to ear, there is similarly enabled the possibility that further signal processing may improve analyses made by stethoscope. As an example may be mentioned that the electronic stethoscope can be adapted to the individual hearing loss of the physician, e.g., by having this measured objectively and converted to a transfer function which is stored in the electronic stethoscope according to the invention. In this connection, there may well be included dynamic limitations so that a certain sound pressure is not exceeded, possibly only in certain frequency bands. It is furthermore advantageous that the sound is brought to the ear as close to the ear canal as possible, in that there is thereby no further influence on the signal which has been corrected in earlier stages. In the case of A/B comparisons between compensated and non-compensated sound such a dynamic limitation will be similarly important.

With a view to prevent disturbing noises during the movement of the measuring transducer of the stethoscope from one place to another, possibly during rubbing on the skin, the stethoscope according to the invention is provided with an automatic amplification control so that the sensitivity of the ear is preserved, because it is not subjected to sudden strong sounds.

As the construction of digital filters is so flexible it becomes simple and economically justifiable to perform an individual adjustment for each of the ears of a physician, in such a way that there are two channels or one multiplexed channel with filters. Apart from this, it will only require two transducers and two pre-amplifiers to obtain a stereophonic electronic stethoscope, as the transducers may be placed such on a body to be examined that the sound production appears spatial through the headphones.

For example, in one embodiment, heart sounds are transformed into a number of spectral components, frequency bands, each representing special features in the signal, such as low frequency beats and relative high frequency murmurs. By means of special filters, these bands are distributed spatial in such a way that beats are localized to the left and murmurs to the right. In another application of the stereophonic electronic stethoscope, the taking of blood pressure can be facilitated by enhancing the characteristics of the phases Korotkoff sounds and by means of an adaptive filter and compressor system built into the stethoscope, thereby helping the physician to distinguish between the phases.

A further improvement of the functionality of the electronic stethoscope were if it can be made hands-free. This is obtained in an advantageous manner in that there is established a wireless (high frequency, low frequency, or optical) link between the transducer part and the head phone part. In this manner listening-in is also enabled, as another listener need only bring his own headphone with receiver for the wireless link. Dependent on the degree of personal signal processing to be performed in the electronic stethoscope, vide supra, the interface between that which is to be inside the central transmitter part and that which is to be inside the headphone is selected at the planning of the system. In order for a system to be complete it will also be relevant to introduce a speech channel, i.e., a microphone with amplifier and transmitter into which the surroundings and the physicians themselves fitted with headphones speak, so that the speech is coupled to the headphones in a wireless fashion, whereby it becomes possible to communicate with the physicians or at least to place emergency calls, even though they are isolated completely from the outside world by the headphones.

Complete hands-free operation will only be possible if the transducer part can remain by itself on the skin of the patient. From in particular neo-natal departments it is known to use straps, but this only creates a proximity, not necessarily a secure and uniform contact to the skin. In connection with the invention it has been found advantageous to adhere the transducer part by means of suction from a small vacuum pump whereby there is also obtained a calibrated distention of the skin, so that a more reproducible contact is obtained. Alternatively, it may be a particular advantage in connection with an acceleration transducer to use a double-faced adhesive strip. Correspondingly, a separate transducer part may be devised in such a way that it may be held under a blood pressure measuring cuff.

Such an improvement in the reproducibility is a prerequisite for obtaining a meaningful result when storing a sound which has been determined during an examination, in order to compare it to a corresponding sound determined later. This sound may be repeated cyclically according to requirements so that weakly represented characteristics may be more easily identified. A series of such sounds may be stored electronically with a view to A/B comparisons. It is quite feasible to store a patient's individual, established sound on a medium which is attached to the file and which may be replayed at a later examination in order that a concrete comparison may be performed and hence a much more precise evaluation of a development, even though several independent physicians might perform the examinations. This sound may equally be stored in the stethoscope itself and may be recalled by entering a code. It would be most relevant to store the unfiltered sound which during comparison is subjected to the same filtering as the direct sound in the stethoscope according to the basic principle of the invention. Correspondingly, it may be expedient to let the stethoscope contain a store for a number of standard sounds which may be recalled for the identification and/or characterization of a new sound.

In case it is desirable to make the transition from a particular stethoscope to the electronic stethoscope particularly unproblematic for the individual physician, his or her private stethoscope may be measured in order to obtain its transfer function, whereupon a filter function closely corresponding to it is established and stored in the electronic stethoscope. A gradual "un-learning" of the set habits may be obtained by also storing a series of corresponding filter functions with gradually less pronounced resonances and anti-resonances, all seen as a gradual transfer to the linear amplification. By performing a training program it will be possible to obtain a complete adjustment to only using linear amplification.

The invention will be described in greater detail with reference to the drawings which show preferred embodiments of the invention by way of example only.

DETAILED DESCRIPTION OF THE INVENTION

Figure 1:
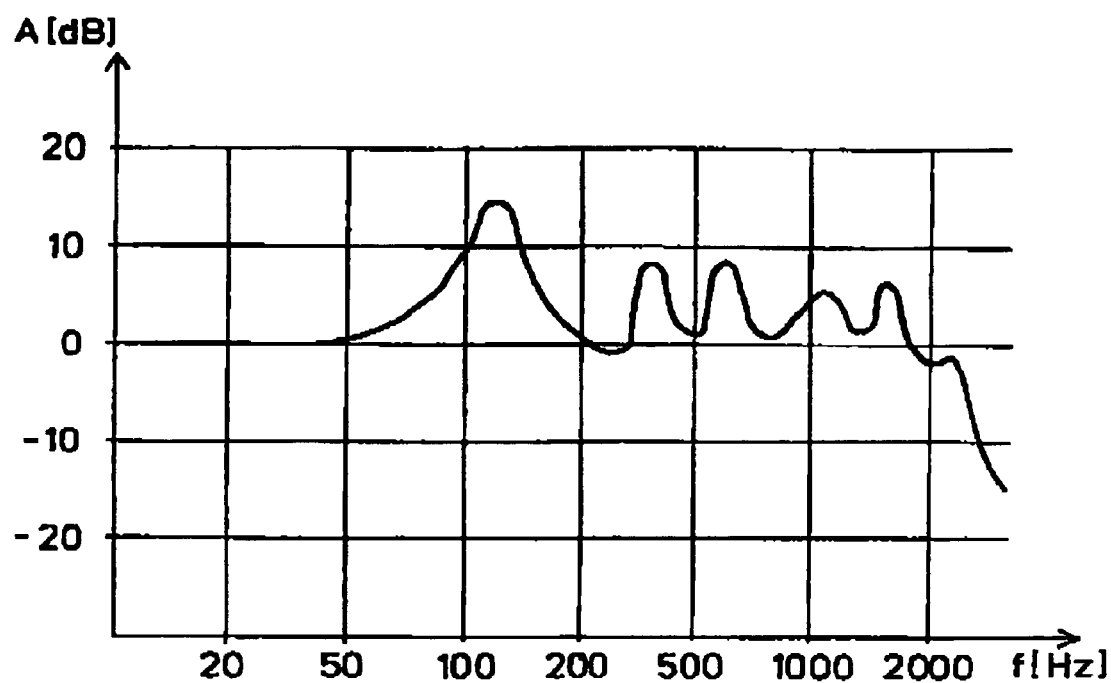
FIG. 1 shows a typical transfer function of a traditional stethoscope.

In FIG. 1 is shown a generalized transfer function for a type of stethoscope which is widely used, i.e., a funnel with two outlets and individual tubes to each ear. It will be seen that there are pronounced resonances and anti-resonances which apart from an amplitude distortion also will give rise to a delay distortion which will make the determination of transients difficult.

Figure 2:
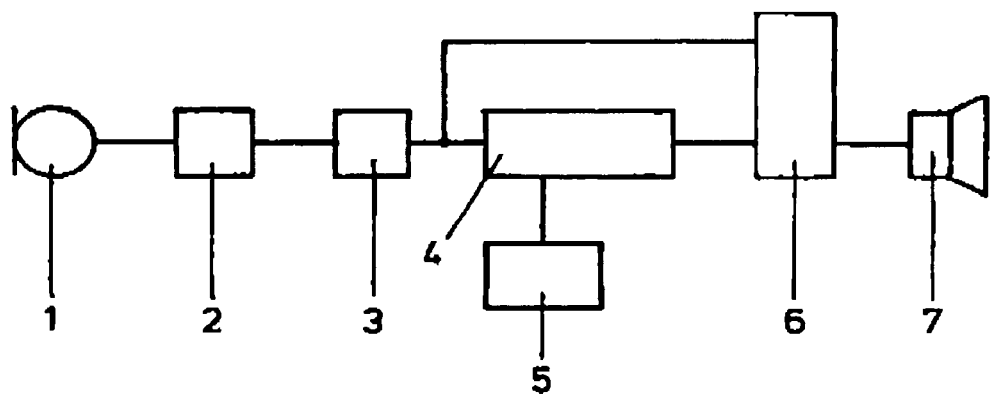
FIG. 2 is a block diagram of a basic principle of a stethoscope according to the invention.

FIG. 2 shows a block diagram for an electronic stethoscope according to the invention. A vibration transducer 1 is used for transferring the signal from the surface of the skin to the apparatus. It may be any kind of transducer, such as a microphone or an accelerometer, i.e., responding to position, velocity or acceleration. A pre-amplifier 2 performs impedance conversion, and pre-emphasis (integration in the case of an accelerometer) takes place in the amplifier 3. There may also be performed a pre-emphasis in dependence of the thickness of fatty and other tissue which is located between the sound source (e.g., the heart) and the transducer. Such pre-emphasis may be as simple as a first order high-pass shelving filter. The choice of transducer is made on the basis of considerations as to signal-to-noise ratio and the pre-emphasis desired. For example, a pre-emphasis filter can be provided for emphasizing high frequencies so as to increase amplification from about 20 Hz to about 3,000 Hz. The unit 4 contains an analog-to-digital converter (A/D converter), a digital filter, and a digital-to-analog converter (D/A converter), in order that a filtered signal may be brought to the output amplifier 6. Furthermore, as shown, there a direct signal is brought from the pre-amplifier 3, in order that an A/B comparison may be made between the signal filtered in 4 and the unfiltered signal. Before such a comparison is performed, there may be a loudness equalization between the two channels so that the comparison will not cause the ear to have too great an adjustment problem. From the output amplifier, the amplified signal is brought to one or several headphones which are only shown as a loudspeaker 7.

In order to be able to switch between several transfer functions for the filter, either different in kind or in principle of the same kind but of less pronounced degree, in store 5, there are stored tables of the filter coefficients needed in order to obtain the desired transfer function for the digital filter. Such a selection of coefficients falls within the general knowledge of the skilled person. It is obvious that other types of digital filter may be selected where the determining parameters are stored in another way than by storing coefficients. One of the transfer functions mentioned may be obtained, not as a representative transfer function of a type of stethoscope, but as the result of a concrete measurement on an individually selected stethoscope.

EXAMPLE

Figure 3:
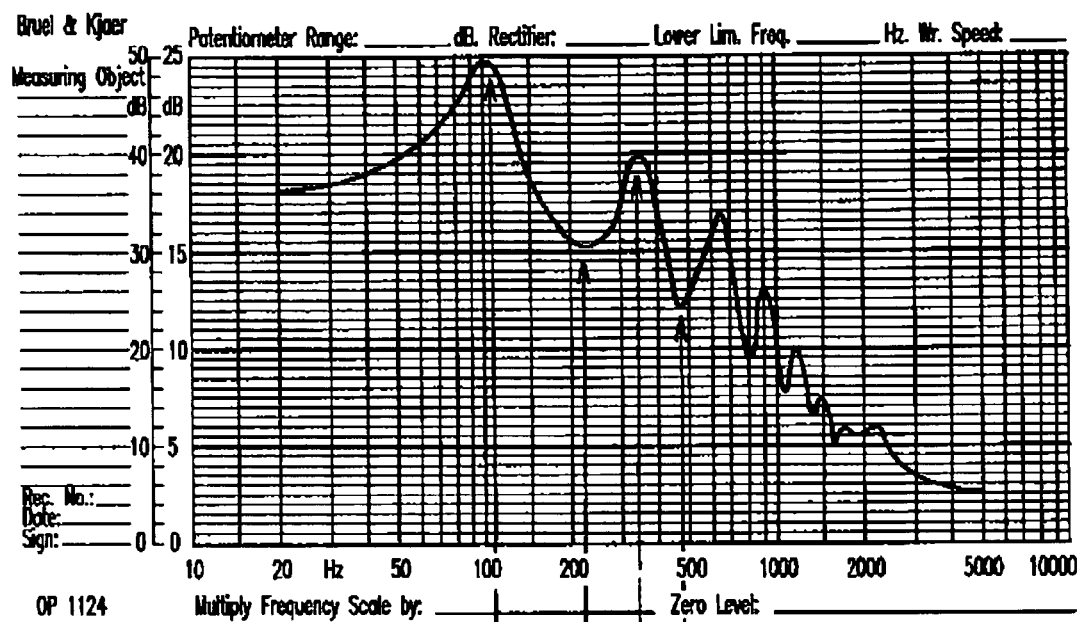
FIG. 3 is a graph representing a transfer function measured from a Littman Classic II stethoscope.

A Littman Classic II stethoscope was measured by two methods. On the one hand, the mechanical dimensions were measured, and the electroacoustic equivalent circuit was developed in the situation where the stethoscope was in contact with the skin as the transmitter and the ear pieces inserted in the ear canal. On the other hand, a unit was measured in a standard Brüel & Kjær acoustic measuring setup with a sweep oscillator and filter and a plotter. FIG. 3 shows the measured transfer function. On the basis of a calculation of the transfer function by means of the electroacoustic equivalent, the filter coefficients for a digital filter were calculated according to standard practice for the first resonance peaks in the transfer function. These coefficients are reproduced in Table 1.

TABLE 1

Filter coefficients for electronic stethoscope (digital filter)

First resonator (2nd order IIR filter)

A0 = 0.167283222079277039
A1 = −0.331625401973724365
A2 = 0.164647430181503296
B0 = 1.000000000000000000
B1 = −1.989778280258178710
B2 = 0.991558074951171875

Second resonator

A0 = 0.168205320835113525
A1 = −0.330643445253372192
A2 = 0.163203150033950806
B0 = 1.000000000000000000
B1 = −1.983934164047241210
B2 = 0.988377273082733154

Third resonator

A0 = 0.167822774839401245
A1 = −0.331159085035324097
A2 = 0.164011687040328980
B0 = 1.000000000000000000
B1 = −1.987000107765197750
B2 = 0.989760994911193848

Fourth resonator

A0 = 0.247263073921203613
A1 = −0.472294241189956665
A2 = 0.232113614678382874
B0 = 1.000000000000000000
B1 = −1.948417305946350100
B2 = 0.977224946022033691

FIR filter (7th order). All coefficients are multiplied by 4!

h(1) = 0.304660081863403320
h(2) = 0.512181341648101807
h(3) = 0.680669605731964111
h(4) = 0.745538234710693359
h(5) = 0.680669605731964111
h(6) = 0.512181341648101807
h(7) = 0.304660081863403320

Figure 4:
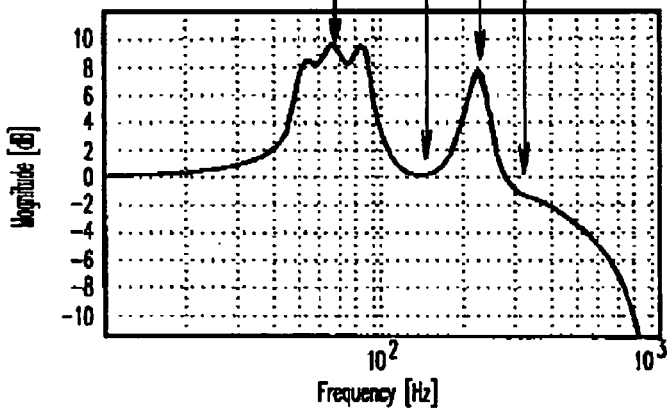
FIG. 4 is a transfer function produced in accordance with the present invention which is equivalent to the measured transfer function of FIG. 3.

The coefficients are stored in a programmable memory device type 27C512 (5 in FIG. 2), and are used in a digital signal processing device type ADSP2101 (4 in FIG. 2). The detailed signal connections between the devices are assumed known to the skilled person. Hereby, the transfer function reproduced in FIG. 4 is obtained. Different units are used on the frequency axes, because the digital signal processing was performed at a clock frequency which deviated from that which would cause the two transfer functions discussed to relate to identical frequency ranges. In the figures, this constant factor has been taken account of, and arrows show the correspondence between resonances and anti-resonances in the measured transfer function and that obtained by digital signal processing.

In a completely analogous manner, the digital filter may be expanded to comprise the resonances and anti-resonances having a smaller amplitude, the filter order being higher. Use of the electroacoustic equivalent circuit as the basis immediately gives the possibility of obtaining a correct impulse response, and an acoustic measurement which also comprises the phase function may be used in a corresponding manner.

Figure 5:
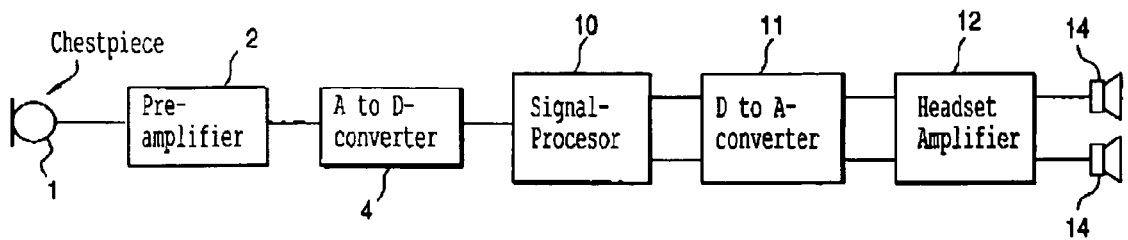
FIG. 5 is a block diagram of an electronic stereo stethoscope according to the invention.

As noted in regard to the prior art, the brain is able to process sounds more effectively when it receives slightly different input from each of the two ears, and this fact has been used to improve audio reproduction of music and for films, i.e., stereo and surround sound vs. monaural sound as well as help jet airplane pilots listen to several communication channels simultaneously by increasing separation via the use of special filters. As also noted, research has been conducted to determine the filter effect of the head (characterized as Head related Transfer Functions, HRTF=s) with regard to sound from two microphones based on distance and source; see, *HRTF Measurements of a KEMAR Dummy-Head Microphone*, Bill Gardner and Keith Martin, MIT Media Lab *Perceptual Computing—Technical Report #280*, May, 1984, (which is hereby incorporated by reference to the extent that it may be necessary to complete an understanding of this invention) and these HRTF=s can be synthesized by digital filters. With this in mind, FIG. 5 shows a block diagram of an electronic stereo stethoscope in accordance with the present invention in which parts corresponding to those of the stethoscope of FIG. 2 bear the same number and serve the same function, so that they need not be described in detail again, signals picked up from vibration transducer 1, after passage through pre-amplifier 2 and A/D converter 4 are processed by signal processor 10 which contains the filters for synthesizing the appropriate HRTF=s and outputs a separate signal for each ear which is passed through D/A convertor 11 and a headset amplifier 12 to left and right earpieces 14.

As be mentioned in the "Summary," the electronic stethoscope can be adapted to the individual hearing loss of the physician, e.g., by having this measured objectively and converted to a transfer function which is stored in the electronic stethoscope according to the invention. This is adjustment is particularly suited to the stereo embodiment since a simple balance control as is known from traditional stereo audio technology may be sufficient to compensate for hearing loss affecting only one ear, or one ear to a greater extent than the other. Furthermore, where both ears are affected by hearing loss, the amplification in each channel should be individually adjustable, or the balance preceded by an adjustable amplification. Still further, where hearing loss affects only certain frequency ranges, such can also be corrected for by means corresponding to conventional equalizer technology as also found in audio equipment. All such adjustments would be implemented before the output driver stage for each ear.

Figure 6A:
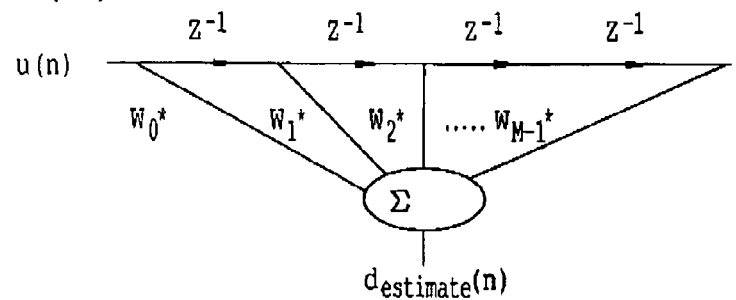
FIGS. 6(a) and 6(b) are representations of the Wiener scenario as applied to synthesis and analysis, respectively, of filters for right and left ears for the electronic stereo stethoscope according to the invention.
Figure 6B:
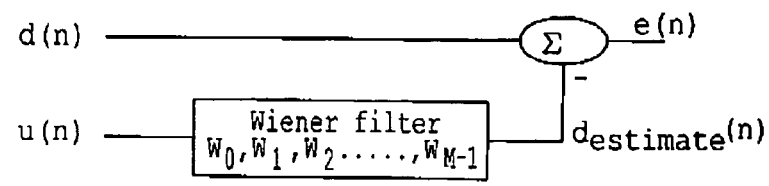

FIGS. 6(a) & 6(b) show one manner in which filters can be used to spatially distribute the sounds delivered to the physician's ears to reflect the angular difference between sounds received by the left and right ears. In particular, either the signal to both ears can be filtered or the original signal can be preserved and sent to one ear. To do so, it is necessary to synthesize the difference at each angle, and this can be done by applying the known Wiener scenario, by which an estimate of the optimal filter coefficients for a specified FIR filter can be arrived at.

In FIGS. 6(a) & 6(b), $d_{estimate}(n)$ designates the impulse response signal $z^{-1}$ to be synthesized for the ear farthest away from the source, and u(n) designates the impulse-response for the other ear, which by proper filtering should mimic $d_{estimate}(n)$. By means of a least mean square algorithm, the coefficients w are adjusted to minimize the error signal e(n). These special filters, one for each angle, are used to arbitrarily place a sound spatially when listening via a stereo headset, the original sound being presented to one ear and a filtered version to the other ear.

Figure 7:
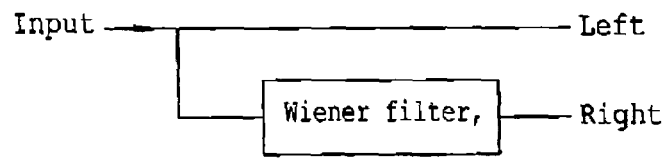
FIGS. 7 & 8 are representations, respectively, of a one and a two band approach to the application of the Wiener scenario to the electronic stereo stethoscope according to the invention.
Figure 8:
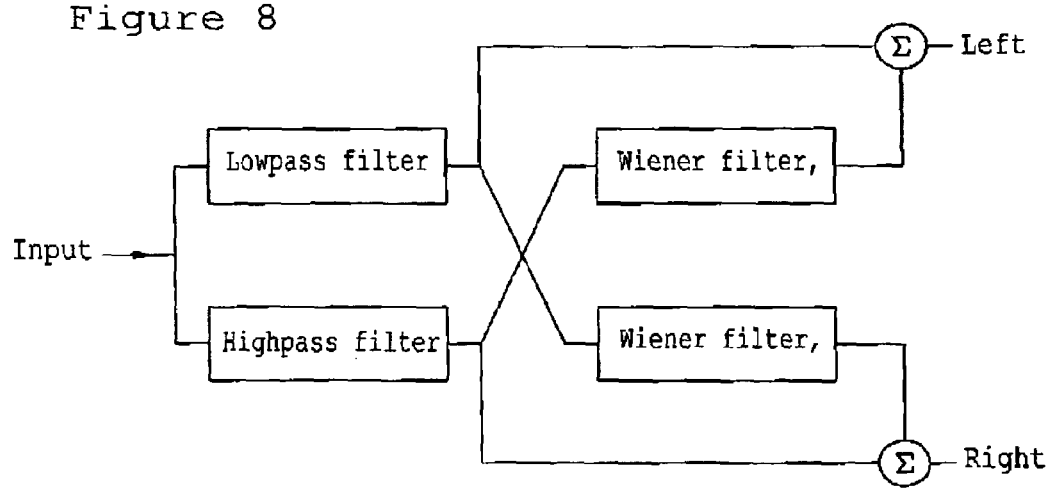

The listening experience can also be expanded by creation of a synthetic listening space in which low frequency sounds, such as heart beats, are perceived as coming from, e.g., the left side while high frequency sounds, such as heart murmurs, from the right side. Similarly, earlier phenomena could be made to appear on, e.g., the left side and subsequent phenomena on the right so that, with a repetitive sequence, there would be a repetition of sounds moving from left to right. In these manners, separating and distinguishing of features is facilitated. FIGS. 7 & 8 represent one band and two band scenarios, respectively, for achieving these effects. In FIG. 7, the input sound passes through to the left ear, while the signal to the right ear is processed in one of the above manners. In FIG. 8, the input sounds are separated and independently process en route to each ear.

Figure 9:
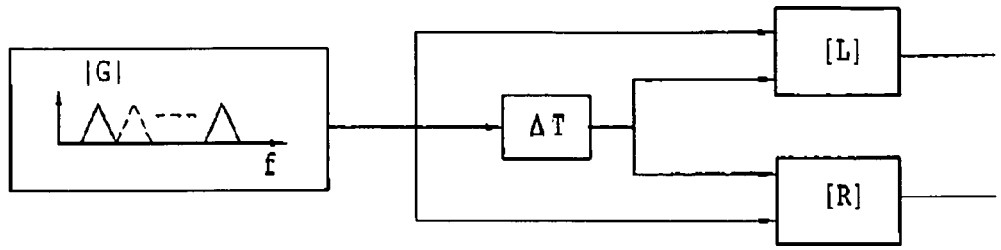
FIG. 9 is a representation of an alternative manner of presenting heart sounds to right and left ears with the electronic stereo stethoscope according to the invention.

FIG. 9 shows an arrangement for transformation of heart sounds from frequency distribution to a spatial distribution. The sound signal is first divided into a number of frequency bands by normal filters or orthogonal filters, orthogonal filters preventing redundancy, which ensures energy preservation. The output from each filter has a direct path and a delayed path to the matrix circuits for the left and right channels. In the matrices, a weighted sum of the input signals is formed in such a way that the lowest to highest frequency bands are perceived as being spatially distributed from left to right, when played back via a stereo speaker system or via a stereo headset. In this way, an alternative presentation can be offered which adds a new dimension to the sound, which apparently enhances the perceived frequency resolution, and by that, the ability to recognize murmurs etc.

Figure 10:
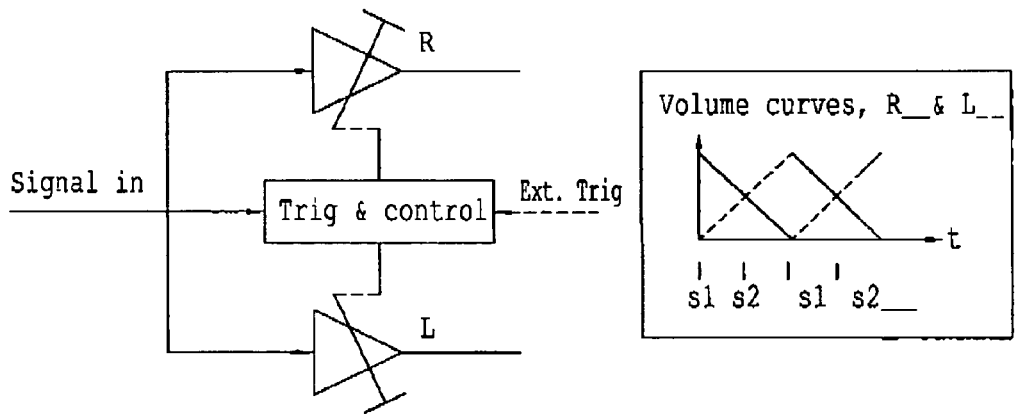
FIG. 10 is a modified embodiment for spatially distributing heart sounds.

FIG. 10, on the other hand, shows an arrangement for the transformation heart sounds from a temporal distribution to a spatial distribution. In this embodiment, the spatial location of the sound follows the temporal location in the heart cycle, from a first heart sound to the next first heart sound, s1 to s1. This means that the systole, s1 to s2, is located on the left side and the diastole, s2 to s1, on the right side. It is like the balance is automatically adjusted with time triggered by a signal derived from the input signal itself or by an external trigger, such as an ECG or the like. In this way, physicians are offered an alternative presentation which is meant to help locate murmurs in the heart cycle, mainly systolic or mainly diastolic.

While the stereoscopic aspect of the invention has been primarily described so far with respect to its use in heart monitoring, it also finds significant applicability in blood pressure measurement. When it comes to blood pressure measurement, the Riva-Rocci method combined with Korotkoff sounds is one of the most widespread today. It makes use of a stethoscope and a sphygmomanometer, which is an inflatable cuff connected to an air pump and a manometer. The cuff is applied around the upper arm and inflated until the radial pulse of the brachial artery disappears. Then, the stethoscope is applied over the artery distal to the cuff, and the air is allowed to deflate slowly, 2–3 mm Hg/s. Korotkoff found that audible sound occurs when the systolic pressure was reached and that the characteristics of the sound changed until diastolic pressure were passed. He categorized these sounds in four phases, —actually he mentioned five phases but the fifth phase is no sound as represented in Table 1.

TABLE 2

| Korotkoff sounds: | Phase 1 | Phase 2 | Phase 3 | Phase 4 | Phase 5 |
| --- | --- | --- | --- | --- | --- |
| Cuff pressure corresponding to: | Systolic pressure Age & sex depen. Typ.: 120 [mmHg] | Cuff pressure between systolic- & diastolic press. | Cuff pressure between systolic- & diastolic press. | Diastolic pressure Age & sex depen. Typ.: 80 [mmHg] | Cuff pressure below diastolic pressure |
| Characteristic of sound: | Tapping sound becomes just audible | Intensity of tapping sound increase | Maximum intensity of tapping sound followed by a brief murmur | Muffled sound | No sound |

Figure 11:
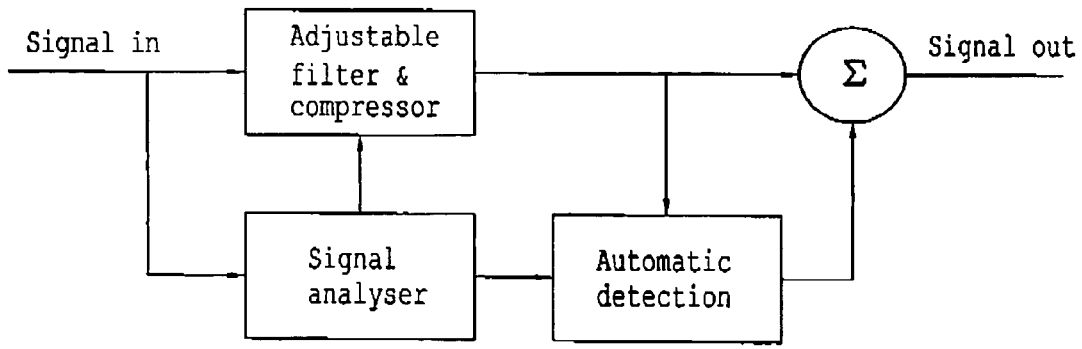
FIG. 11 is a diagram illustrating a sound enhancing arrangement for the electronic stereo stethoscope according to the invention particularly suited for blood pressure measurement.

The present invention enables the characteristics in the different phases to be enhanced by means of an adaptive filter and compressor system built into an electronic stethoscope so as to help physicians to distinguish between the phases and thereby make more accurate measurements. Automatic detection can be an option, signalled by a beep sound superimposed on the sound channel. FIG. 11 diagrammatically depicts such an embodiment.

From the foregoing, it should be apparent how the present invention provides a simple and reliable means for not only electronically emulating any analog stethoscope, but also increase the easier for a physician to accurately and reliability of monitor body functions via a stethoscope.

While various embodiments in accordance with the present invention have been shown and described, it is understood that the invention is not limited thereto, and is susceptible to numerous changes and modifications as known to those skilled in the art. Therefore, this invention is not limited to the details shown and described herein, and includes all such changes and modifications as are encompassed by the scope of the appended claims.

What is claimed is:

1. An electronic digital stethoscope comprising a single vibration transducer for creating a single channel input signal, an amplifier, a headphone arrangement, a pre-emphasis filter means for emphasizing high frequencies, and at least one digital filter means for establishing at least one impulse transfer function corresponding to at least one acoustic stethoscope type; wherein said pre-emphasis means comprises a high-pass shelving filter for increasing amplification prior to establishment of the at least one impulse transfer function by said at least one digital filter means, said shelving filter having a shelving limit at about 3,000 Hz.

2. A stethoscope according to claim 1, further comprising means for automatic control of amplification.

3. A stethoscope according to claim 1, wherein the headphone arrangement comprises transducers which are fitted in immediate proximity to the ear canal in each ear.

4. A stethoscope according to claim 3, wherein the signal to each ear is compensated with respect to the sensitivity of the particular earpiece.

5. An electronic digital stethoscope comprising a vibration transducer, an amplifier, a headphone arrangement, a pre-emphasis filter means for emphasizing high frequencies, and at least one digital filter means for establishing at least one impulse transfer function corresponding to at least one acoustic stethoscope type; further comprising means for performing a comparison between the unfiltered linear sound and the sound after digital filtering.

6. An electronic digital stethoscope comprising a vibration transducer, an amplifier, a headphone arrangement, a pre-emphasis filter means for emphasizing high frequencies up to about 3,000 Hz, and at least one digital filter means for establishing at least one impulse transfer function corresponding to at least one acoustic stethoscope type; wherein multiple sets of coefficients for producing multiple impulse transfer functions corresponding to multiple acoustic stethoscope types are stored in conjunction with the digital filter.

7. An electronic digital stethoscope comprising a vibration transducer, an amplifier, a headphone arrangement, a pre-emphasis filter means for emphasizing high frequencies, and at least one digital filter means for establishing at least one impulse transfer function corresponding to at least one acoustic stethoscope type and being located for receiving a signal after it has been processed by said pre-emphasis filter means; wherein said pre-emphasis means is operative for increasing amplification, wherein the at least one impulse transfer function of the digital filter means is obtained by measurement on a specific acoustic stethoscope type, the type categorized other than by noise reduction.

8. An electronic digital stethoscope comprising a single vibration transducer for creating a single channel input signal, an amplifier, a headphone arrangement, a pre-emphasis filter means for emphasizing high frequencies of said single channel input signal, and at least one digital filter means for establishing at least one impulse transfer function corresponding to at least one acoustic stethoscope type; wherein said pre-emphasis means is operative for increasing amplification, further comprising digital pattern recognition means for windowing the acoustic signal to adaptively remove noise from the surroundings and suppress repetitive signals in the observed signal.

9. A stethoscope according to claim 8, wherein the pattern recognition means is adapted to remove or enhance parts of repetitive signals in the observed signal.

10. An electronic digital stethoscope comprising a vibration transducer, an amplifier, a headphone arrangement, a pre-emphasis filter means for emphasizing high frequencies by increasing amplification, and at least one digital filter means for establishing at least one impulse transfer function corresponding to at least one acoustic stethoscope type; wherein said pre-emphasis filter is located in the signal path before said at least one digital filter means, and for pre-emphasis of the high frequencies, acts in dependence of the thickness of tissue which is present between an actual sound source and the transducer.

11. An electronic digital stethoscope comprising a vibration transducer, an amplifier, a headphone arrangement, a pre-emphasis filter means for emphasizing high frequencies, and at least one digital filter means for establishing at least one impulse transfer function corresponding to at least one acoustic stethoscope type; further comprising signal processing means for producing a sound distribution to the headphone in which different sound signals are sent to each of left and right ears of a user.

12. A stethoscope according to claim 11, wherein said at least one filter means comprise plural filters which produce a spatial sound distribution based on frequency, a low frequency band being delivered to a first earpiece of the headphone and a high frequency band being delivered to a second earpiece of the headphone.

13. A stethoscope according to claim 11, wherein said signal processing means produces a temporal sound distribution, sound signals being first being delivered to a first earpiece of the headphone and then being delivered to a second earpiece of the headphone.

14. A stethoscope according to claim 11, wherein said signal processing means produces a temporal sound distribution, sound signals being alternately delivered to a first earpiece of the headphone and to a second earpiece of the headphone.

15. A stethoscope according to claim 11, wherein said at least one filter means comprise at least one Wiener filter.

16. A stethoscope according to claim 11, wherein balance control means is provided adjusting the relative volume of sound delivered to each ear of a user.

17. A stethoscope according to claim 16, wherein frequency-dependent amplification control means is provided for adjusting the volume of sound delivered to one ear of a user relative to that delivered to the other ear of the user.

18. A stethoscope according to claim 11, wherein amplification control means is provided adjusting the volume of sound delivered to one ear of a user relative to that delivered to the other ear of the user.

* * * * *